United States Patent
Stohr

(10) Patent No.: US 10,441,741 B2
(45) Date of Patent: Oct. 15, 2019

(54) METHOD TO IMPROVE DIGESTION ACOUSTICALLY

(71) Applicant: Luis Stohr, Redondo Beach, CA (US)

(72) Inventor: Luis Stohr, Redondo Beach, CA (US)

(73) Assignee: Gadgets Trend LLC, Redondo Beach, CA (US)

(*) Notice: Subject to any disclaimer, the term of this patent is extended or adjusted under 35 U.S.C. 154(b) by 308 days.

(21) Appl. No.: 15/597,898

(22) Filed: May 17, 2017

(65) Prior Publication Data

US 2018/0085550 A1 Mar. 29, 2018

Related U.S. Application Data

(60) Provisional application No. 62/401,593, filed on Sep. 29, 2016.

(51) Int. Cl.
*A61M 21/00* (2006.01)
*H05B 37/02* (2006.01)
*G05B 19/12* (2006.01)
*G06Q 10/02* (2012.01)
*H04W 4/02* (2018.01)
*H04W 4/08* (2009.01)
*H04M 1/22* (2006.01)

(52) U.S. Cl.
CPC ......... *A61M 21/00* (2013.01); *H05B 37/0227* (2013.01); *A61M 2021/0027* (2013.01); *G05B 19/124* (2013.01); *G05B 2219/23039* (2013.01); *G05B 2219/23406* (2013.01); *G06Q 10/02* (2013.01); *H04M 1/22* (2013.01); *H04W 4/02* (2013.01); *H04W 4/08* (2013.01)

(58) Field of Classification Search
CPC .......... A61M 21/00; A61M 2021/0005; A61M 2021/0027; A61M 2021/0022
See application file for complete search history.

(56) References Cited

U.S. PATENT DOCUMENTS

2013/0096368 A1* 4/2013 Devroey .................. A61B 5/11
600/28

* cited by examiner

*Primary Examiner* — Kaylee R Wilson
(74) *Attorney, Agent, or Firm* — Che-Yang Chen; Law Offices of Scott Warmuth

(57) ABSTRACT

A method to improve digestion for an individual, especially the digestion issue caused by the individual's mental issues, may include steps of choosing one or more individuals having digestive discomfort caused by mental issues that may happen periodically; generating a sound file of digestion sounds for a predetermined length of time; administrating the sound file to the individual for a predetermined period of time; and determining if the individual's digestion is improved. In one embodiment, the step of generating a sound file of digestion sounds may include steps of recording the digestion sounds from a person during good digestion and editing the digestion sounds. In another embodiment, the predetermined length of time can be ten minutes.

3 Claims, 6 Drawing Sheets

METHOD TO IMPROVE DIGESTION ACOUSTICALLY

CROSS-REFERENCE TO RELATED APPLICATIONS

This application claims priority under 35 U.S.C. § 119 (e) to U.S. Provisional Patent Application Ser. No. 62/401,593, filed on Sep. 26, 2016, the entire contents of which are hereby incorporated by reference.

FIELD OF THE INVENTION

The present invention relates generally to a method to improve digestion, and more particularly to a method to improve digestion by providing a pre-recorded sound of digestive process.

BACKGROUND OF THE INVENTION

Stress and appetite have an unusual connection. Each person responds to anxiety differently, but many people find that their anxieties cause them to develop appetite problems that affect not only the way they eat, but also the way they enjoy food. But if you're suffering from anxiety symptoms, there is no doubt that your appetite is affected somehow.

Appetite problems are never a standalone symptom. In fact, most people don't realize they have much of an appetite issue. They simply notice that they're eating differently while they deal with other anxiety symptoms. Appetite shouldn't be confused with digestion. Anxiety does cause digestion issues as well, but these are usually caused by other issues. For example, anxiety may make some people eat more or eat less. Some people go straight to food when they are stressed. While it's not clear what develops this issue, the reason for it is well known. When some people eat, they experience a flood of positive neurotransmitters—brain chemicals that cause them to feel good. Food and eating becomes a coping mechanism, so whenever these people become stressed they become hungry. Eventually, the idea of eating when stressed becomes conditioned. Namely, the body trains itself to crave food when it's suffering from anxiety.

On the other hand, anxiety may make people eat less. The reason why anxiety reduces hunger in some people maybe because the excess stomach acids simply create the "full" feeling for longer, and chemicals that signal hunger no longer reach the brain. Also, Serotonin or other of the different hormones and neurotransmitters are related to anxiety, digestion, and hunger, and all of these may be telling people's brain that you don't need to eat even though you're otherwise hungry.

Digestion is controlled by the enteric nervous system, a system composed of hundreds of millions of nerves that communicate with the central nervous system. When stress activates the "flight or fight" response in your central nervous system, digestion can shut down because your central nervous system shuts down blood flow, affects the contractions of your digestive muscles, and decreases secretions needed for digestion. Stress can cause inflammation of the gastrointestinal system, and make you more susceptible to infection.

Moreover, stress can cause the esophagus to go into spasms and can increase the acid in your stomach causing indigestion. Under stress, the mill in an individual stomach can shut down and make the individual feel nauseous. Stress can cause the individual's colon to react in a way that causes diarrhea or constipation. We are all familiar with the athlete or the student who has to rush to the bathroom before the big game or the big exam.

Common indigestions on individuals (humans or animals) are caused by an interruption of the digestive process. In some cases because there is an anomaly that might not be created by the food itself or the digestive system but by the individual mental stage, such as nervousness, stress, insomnia, etc. These digestion anomalies are pacified through chemical approaches such as anti-acid medicines, ulcer preventive medicines, and other substances. However, the individual may feel uncomfortable after taking the medicines, and the medicines may even generate some side effects to some individuals. Therefore, there remains a need for a new and improved method to treat digestion anomalies and overcome the problems stated above.

SUMMARY OF THE INVENTION

It is an object of the present invention to provide a method to treat digestion discomfort instead of using medicines.

It is another object of the present invention to provide a method to take an individual's digestive sound and use it to treat digestion discomfort that may cause by the individual's mental issues.

It is a further object of the present invention to provide a method to improve an individual's digestion discomfort and the effect of the improvement can be quantitatively measured.

Digestive sounds produced by humans and animals during hunger or digesting food is recorded and played back by a speaker exposed right at the digestive organs area or heard by headphones, creating vibration that can be perceived acoustically too. These sounds will send messages to the individual brain that the digestion is going through, so if the brain stopped the digestion process by mental reasons, the brain will release a "go" message to the digestion system and continue the digestive stages without interruptions.

In one aspect, a method to improve digestion for an individual, especially the digestion issue caused by the individual's mental issues, may include steps of choosing one or more individuals having digestive discomfort caused by mental issues that may happen periodically; generating a sound file of digestion sounds for a predetermined length of time; administrating the sound file to the individual for a predetermined period of time; and determining if the individual's digestion is improved.

In one embodiment, the step of generating a sound file of digestion sounds may include steps of recording the digestion sounds from a person during good digestion and editing the digestion sounds. In another embodiment, the step of determining if the individual's digestion is improved may include a step of observing if the individual is hungry and eats regularly after being administrated to the sound file.

DETAILED DESCRIPTION OF THE INVENTION

Figure 1:
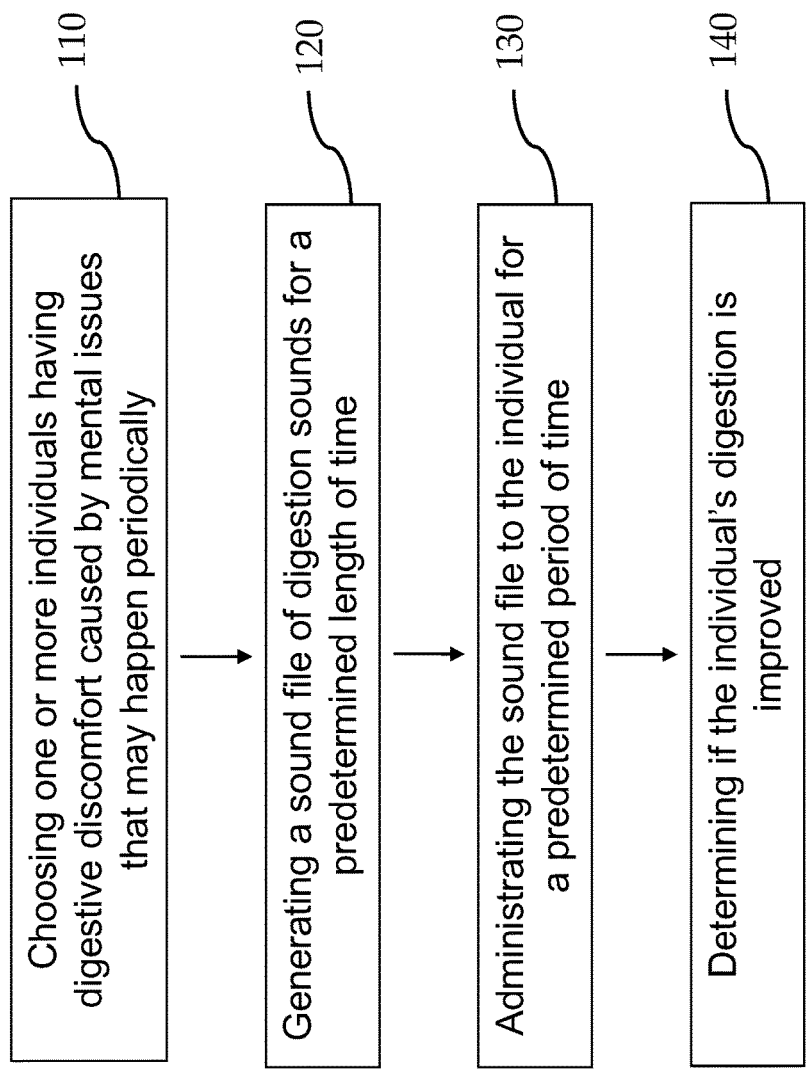
FIG. 1 illustrates a method to improve digestion for an individual in the present invention.

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

All publications mentioned are incorporated by reference for the purpose of describing and disclosing, for example, the designs and methodologies that are described in the publications that might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

As used in the description herein and throughout the claims that follow, the meaning of "a", "an", and "the" includes reference to the plural unless the context clearly dictates otherwise. Also, as used in the description herein and throughout the claims that follow, the terms "comprise or comprising", "include or including", "have or having", "contain or containing" and the like are to be understood to be open-ended, i.e., to mean including but not limited to. As used in the description herein and throughout the claims that follow, the meaning of "in" includes "in" and "on" unless the context clearly dictates otherwise.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the embodiments. As used herein, the term "and/or" includes any and all combinations of one or more of the associated listed items.

Regular hunger or digesting food process has sounds created by gastric fluids going through the stomach and intestines. When these sounds are played back during a digestion interruptions caused by mental situations, these sounds will emulate the efficient digestion sounds so subjectively contribute to improve the digestion of the individual.

Digestive sounds produced by humans and animals during hunger or digesting food is recorded and played back by a speaker exposed right at the digestive organs area or heard by headphones, creating vibration that can be perceived acoustically too. These sounds will send messages to the individual brain that the digestion is going through, so if the brain stopped the digestion process by mental reasons, the brain will release a "go" message to the digestion system and continue the digestive stages without interruptions.

The presented invention creates a new approach to improve individuals' digestion complications by exposing them to pre-recorded efficient digestive process sound that will be exposed through hearing and/or acoustic vibrations on the gastric organs areas, making the individuals perceive efficient digestion stages. Even if the digestion is not as efficient, the subconscious of the individuals will still send the message to continue the digestive process.

In one aspect, a method to improve digestion for an individual, especially the digestion issue caused by the individual's mental issues, may include steps of choosing one or more individuals having digestive discomfort caused by mental issues that may happen periodically 110; generating a sound file of digestion sounds for a predetermined length of time 120; administrating the sound file to the individual for a predetermined period of time 130; and determining if the individual's digestion is improved 140.

In one embodiment, the step of generating a sound file of digestion sounds may include steps of recording the digestion sounds from a person during good digestion 121 and editing the digestion sounds 122. In another embodiment, the predetermined length of time in step 120 can be ten minutes. In a further embodiment, the step of determining if the individual's digestion is improved 140 may include a step of observing if the individual is hungry and eats regularly after being administrated to the sound file 141.

EXPERIMENT I

Figure 2:
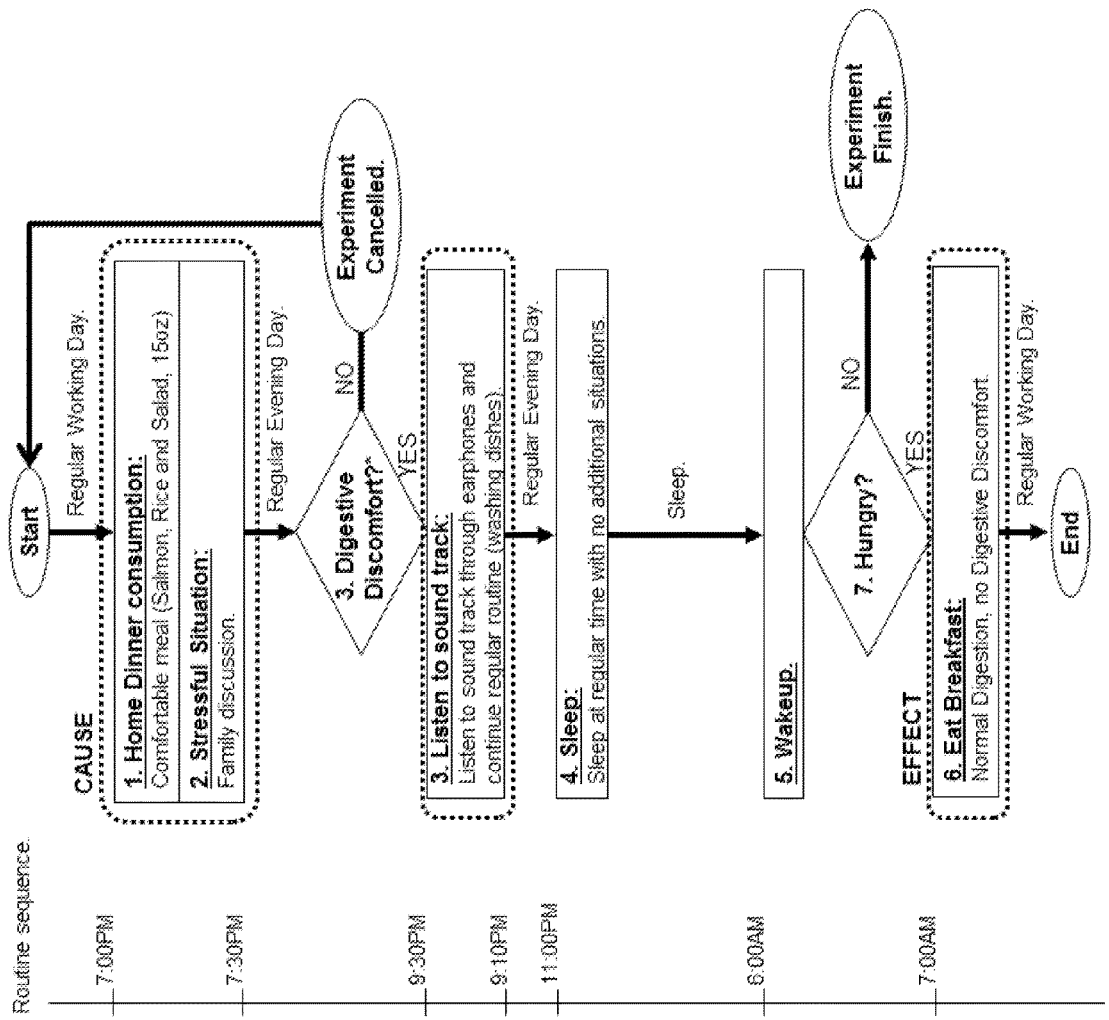
FIG. 2 is a flow diagram and timeline of the first person who was administered the sound file to improve digestion in the present invention.

A number of experiments have been conducted on individuals who suffered from digestion discomfort. As shown in FIG. 2, the first person had a regular dinner at around 7 pm one day and became stressful after dinner when hearing about some family issues. The first person started to feel some digestion discomfort after dinner and the sound file developed in step 120 in the present invention is administered through the earphone at about 9:30 pm for about 10-20 minutes before sleep. The first person woke up at 6 am the next day and the digestion discomfort seemed to disappear so she can eat breakfast as normal.

EXPERIMENT II

Figure 3:
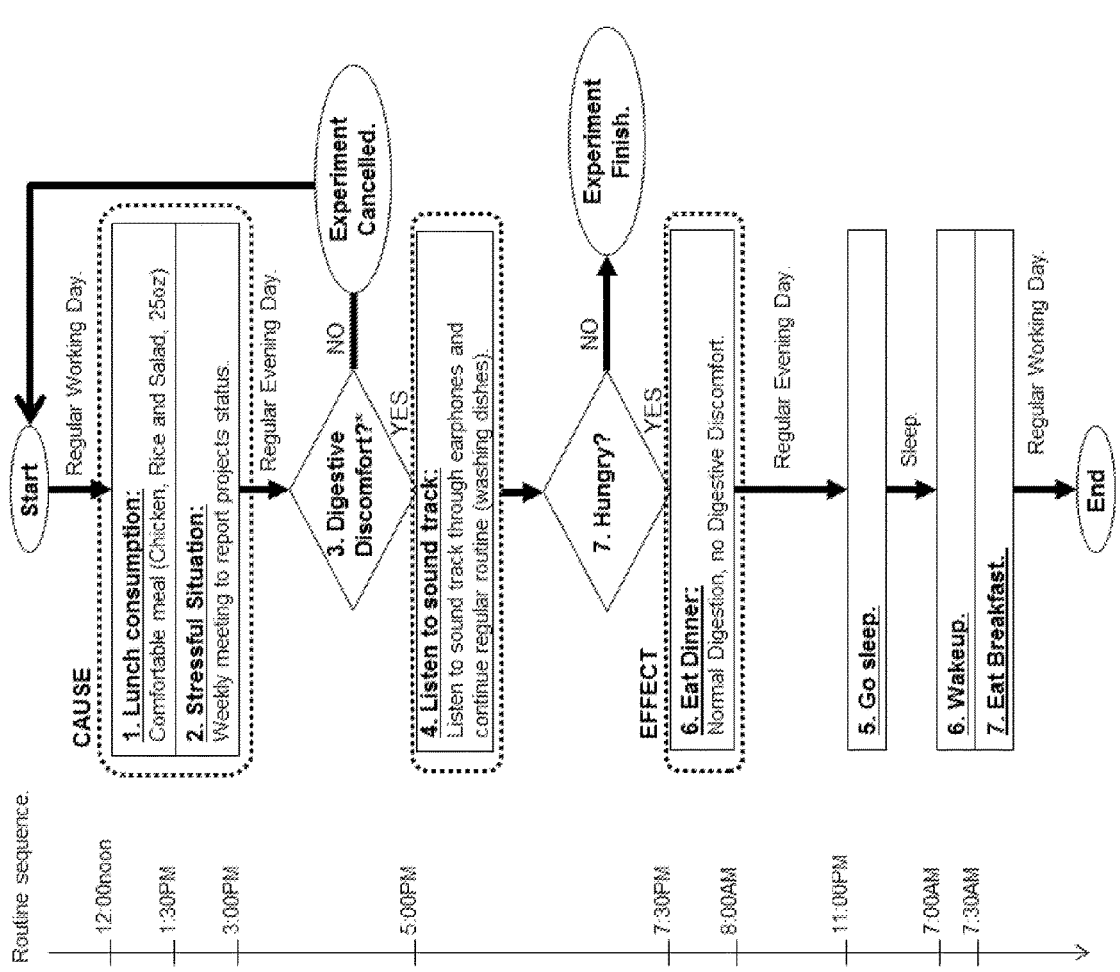
FIG. 3 is a flow diagram and timeline of the second person who was administered the sound file to improve digestion in the present invention.

As shown in FIG. 3, the second person's stressful situation started after a regular lunch when there was a weekly meeting to report projects status. The second person started to feel digestion discomfort after the meeting and the sound file generated in step 120 was provided to the second person for about 10-20 minutes at about 5 pm on that day.

After listening to the sound file, the person seemed to feel better and was able to eat dinner at around 7:30 pm with no digestive discomfort and go the sleep at around 11 pm. Everything seemed normal to the second person who can also eat breakfast the next day without digestion discomfort.

The improvement of digestion in the present invention can not only be observed, but also identified quantitatively. If an individual with indigestion and exposed to sound track developed in the present invention shows improvement on digestion, the individual may feel hungry thereafter, which means that the digestive system empty the esophagus and small intestines starts absorbing as a regular digestive process.

More specifically, when digestion starts inside the individual, bacterial chemical reaction occurs at the small intestine, creating as a result of the release of Hydrogen molecules that are transported to the lungs through the blood and expelled with $CO_2$ outside the individual when breathing. If this hydrogen can be measured, it is possible to define the digestion that starts in the individual. If the digestion is faster when the individual is exposed to the sound file than not exposed to the sound file, it can be proved that the sound file has the influence to improve the individual's digestion.

Figure 4A:
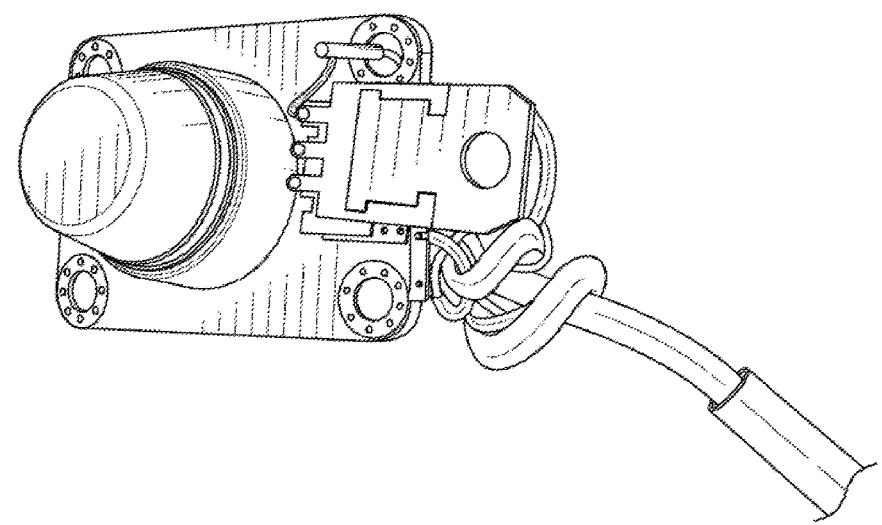
FIGS. 4 and 4a illustrate devices to measure hydrogen level of an individual to determine if the sound file developed in the present invention improves the digestion.
Figure 4:
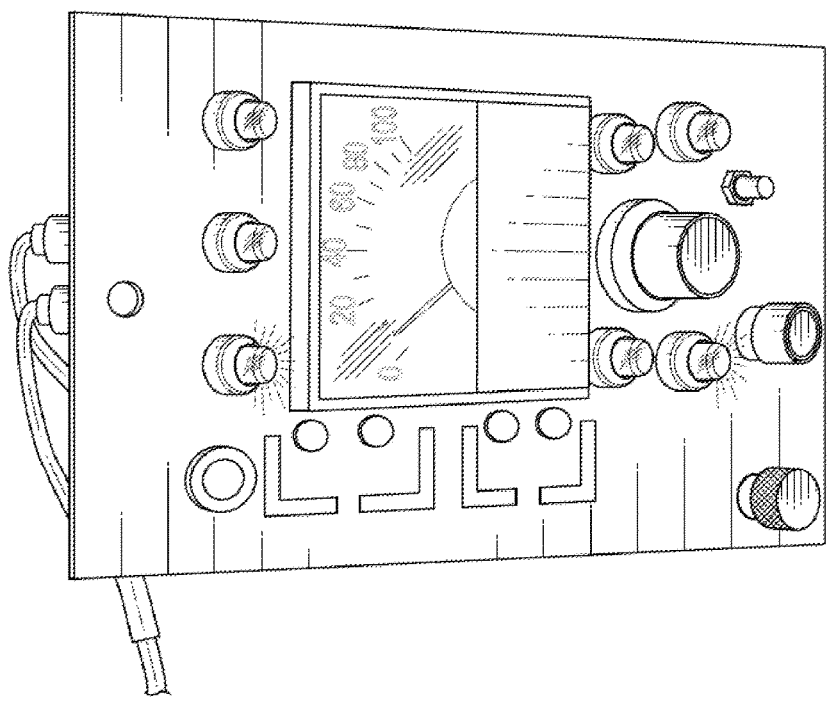

In one embodiment, the apparatus to measure the hydrogen expelled from the individual is an "International Sensor Technology" meter combined with a "V2" gas sensor for hydrogen as shown in FIGS. 4 and 4a respectively. When the measurement of hydrogen is conducted, the individual inhales and exhales slowly with the V2 sensor between 1 cm and 2 cm in front of the mouth, and the hydrogen level of the individual's breath can be recorded as shown in FIGS. 5 and 6.

Figure 5:
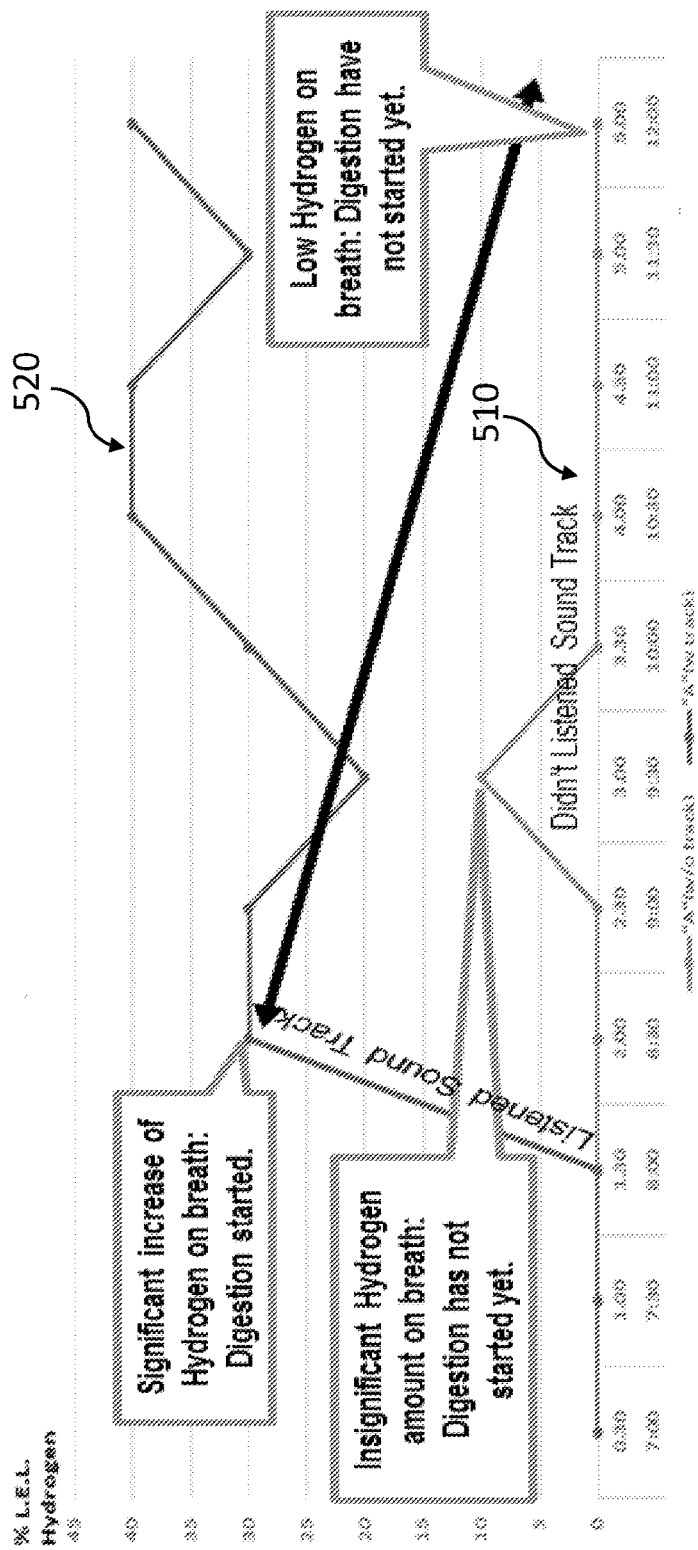
FIG. 5 shows the hydrogen level of the first person who was administered the sound file to improve digestion in the present invention.

More specifically, two hydrogen levels 510 and 520 are shown in FIG. 5 for the first person in Experiment I, wherein the hydrogen level 510 indicates an insignificant hydrogen amount on breath, which means the digestion has not yet started. Also, it is noted that the first person has not yet listened to the sound file developed in step 120.

As stated in Experiment I, the first person was provided with the sound file developed in step 120 in the present invention after feeling digestion discomfort after dinner, and around 9:30 pm a rising hydrogen level can be seen in 520. It is noted that the hydrogen level detected in the first person after being administered the sound file is much higher than the hydrogen level when the digestion has not yet started. Namely, the sound file developed in the present invention can really improve the digestion for the individual.

Figure 6:
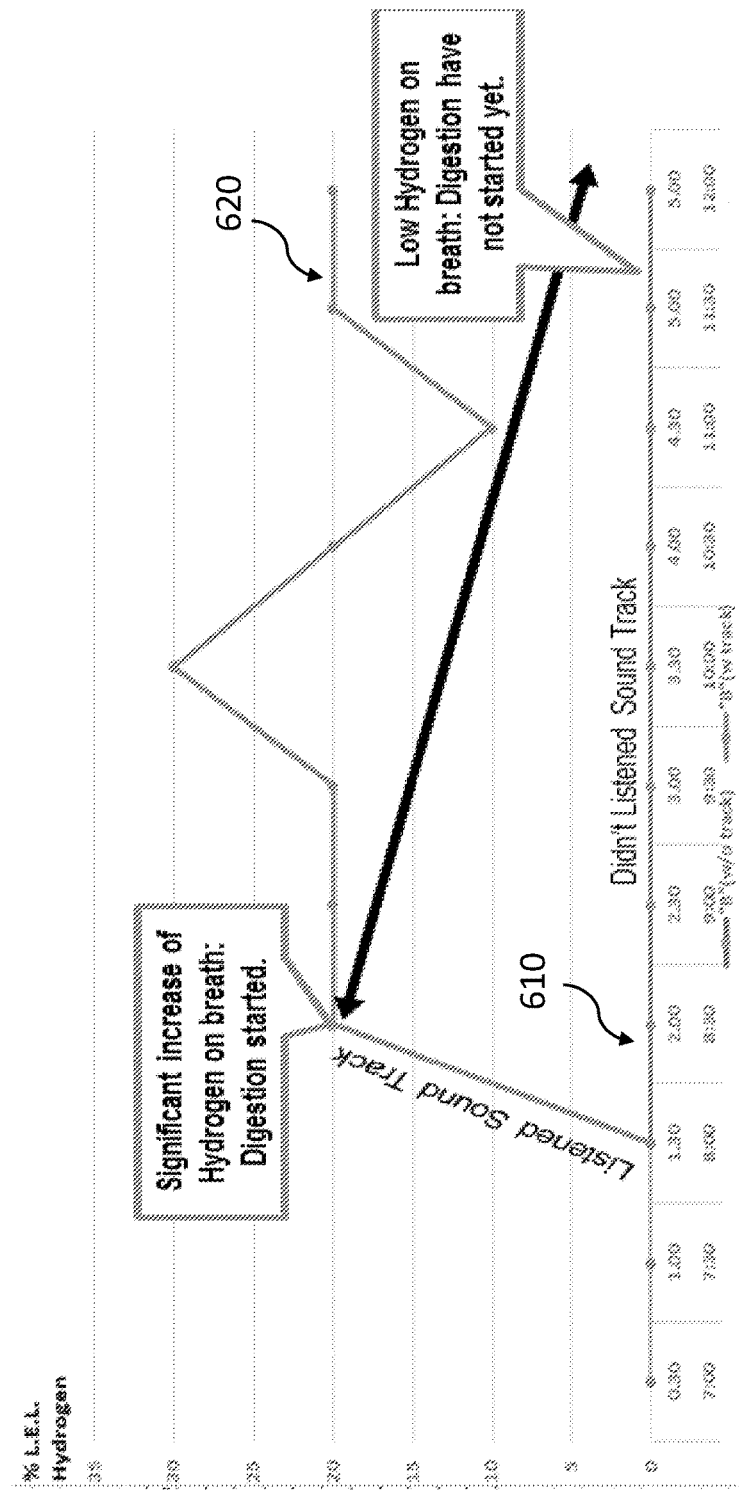
FIG. 6 shows the hydrogen level of the second person who was administered the sound file to improve digestion in the present invention.

The same rising hydrogen level can be found in FIG. 6 as well. As stated in Experiment II, the second person started to feel digestion discomfort after the meeting around 3 pm and was administered the sound file after feeling digestion discomfort, and at around 5 pm and the rising hydrogen level can be seen in 620. Similar to line 520, the hydrogen level detected in the second person after being administered the sound file is much higher than the hydrogen level when the digestion has not yet started (line 610). Namely, the sound file developed in the present invention can really improve the digestion of the individual.

Having described the invention by the description and illustrations above, it should be understood that these are exemplary of the invention and are not to be considered as limiting. Accordingly, the invention is not to be considered as limited by the foregoing description, but includes any equivalents.

What is claimed is:

1. A method for improving digestion for an individual comprising steps of choosing one or more individuals having digestive discomfort caused by mental issues that may happen periodically; generating a sound file of digestion sounds for a predetermined length of time; administrating the sound file to the one or more individuals for a predetermined period of time; and determining if the one or more individual's digestion is improved by measuring a hydrogen level of the one or more individual's breath.

2. The method for improving digestion for an individual of claim 1, wherein the step of generating a sound file of digestion sounds includes steps of recording the digestion sounds from a person during good digestion and editing the digestion sounds.

3. The method for improving digestion for an individual of claim 1, wherein the predetermined length of time of the sound file is ten minutes.

* * * * *